(12) United States Patent
Hu

(10) Patent No.: US 7,920,252 B2
(45) Date of Patent: Apr. 5, 2011

(54) METHOD AND APPARATUS FOR SPECTROPHOTOMETRIC CHARACTERIZATION OF TURBID MATERIALS

(76) Inventor: Xin Hua Hu, Greeivlle, NC (US)

( * ) Notice: Subject to any disclaimer, the term of this patent is extended or adjusted under 35 U.S.C. 154(b) by 202 days.

(21) Appl. No.: 12/250,611

(22) Filed: Oct. 14, 2008

(65) Prior Publication Data

US 2009/0103085 A1   Apr. 23, 2009

(30) Foreign Application Priority Data

Oct. 19, 2007   (CN) .............................. 2007 1 005994

(51) Int. Cl.
*G01J 3/42* (2006.01)
(52) U.S. Cl. .......................................... 356/73; 356/319
(58) Field of Classification Search .................... 356/73, 356/319
See application file for complete search history.

*Primary Examiner* — F. L Evans

(57) ABSTRACT

Method and apparatus for spectrophotometric characterization of turbid materials are provided. An incident light beam is used to illuminate a turbid material sample and optical signals of coherent reflectance, diffuse reflectance, collimated transmittance and diffuse transmittance are measured from the sample as functions of wavelength. The following optical parameters are determined as functions of wavelength for spectrophotometric characterization of the turbid material sample in the spectrum of interest: absorption coefficients $\mu_a$, scattering coefficient $\mu_s$, anisotropy factor g and real refractive index n.

19 Claims, 6 Drawing Sheets

METHOD AND APPARATUS FOR SPECTROPHOTOMETRIC CHARACTERIZATION OF TURBID MATERIALS

LITERATURE REFERENCES

[1] H. C. van de Hulst, Multiple light scattering: tables, formulas, and applications (Academic Press, New York, 1980), Vol. 1 & 2.

[2] H. Ding, J. Q. Lu, K. M. Jacobs, and X. H. Hu, "Determination of refractive indices of porcine skin tissues and intralipid at eight wavelengths between 325 and 1557 nm," J. Opt. Soc. Am. A 22, 1151-1157 (2005).

[3] L. G. Henyey and J. L. Greenstein, "Diffuse radiation in the galaxy," Astrophys J 93, 70-83 (1941).

[4] V. G. Peters, D. R. Wyman, M. S. Patterson, and G. L. Frank, "Optical properties of normal and diseased human breast tissues in the visible and near infrared," Phys. Med. Biol. 35, 1317-1334 (1990).

[5] S. A. Prahl, M. J. C. van Gemert, and A. J. Welch, "Determining the optical properties of turbid media by using the adding-doubling method," Appl. Opt. 32, 559-568 (1993).

[6] I. V. Yaroslavsky, A. N. Yaroslavsky, T. Goldbach, and H.-J. Schwarzmaier, "Inverse hybrid technique for determining the optical properties of turbid media from integrating-sphere measurements," Appl. Opt. 35, 6797-6809 (1996).

[7] C. K. Hayakawa, B. Y. Hill, J. S. You, F. Bevilacqua, J. Spanier, and V. Venugopalan, "Use of the delta-P1 approximation for recovery of optical absorption, scattering, and asymmetry coefficients in turbid media," Appl. Opt. 43, 4677-4684 (2004).

[8] C. Chen, J. Q. Lu, H. Ding, K. M. Jacobs, Y. Du, and X. H. Hu, "A primary method for determination of optical parameters of turbid samples and application to intralipid between 550 and 1630 nm," Opt. Express 14, 7420-7435 (2006).

[9] Z. Song, K. Dong, X. H. Hu, and J. Q. Lu, "Monte Carlo simulation of converging laser beams propagating in biological materials," Appl. Opt. 38, 2944-2949 (1999).

FIELD OF THE INVENTION

The present invention relates to a new type of spectrophotometers for characterization of turbid materials by determining their optical parameters of an absorption coefficient, a scattering coefficient, an anisotropy factor and a real refractive index as functions of wavelength in the spectrum of interest.

BACKGROUND OF THE INVENTION

Spectrophotometer is one of the most widely used analytical instruments to characterize materials in research, development and industrial applications. Existing spectrophotometers, however, lack the ability to accurately characterize materials with different types of turbidity. A material is defined as turbid if it exhibits light scattering in which the scattered light has the same wavelength as that of the incident light. Many natural and artificial materials are of different degrees of turbidity which include polluted water, contaminated oil, paint, milk, blood, aqueous suspensions of biological cells and/or nanoparticles, biological and human tissues. Many of these materials exhibit strong light scattering characteristics, in addition to light absorption, in their interaction with light in the optical spectrum from ultraviolet to infrared.

One of the most accurate optical models to characterize light absorption and scattering in turbid materials is provided by combining the radiative transfer (RT) theory to describe light transportation in a turbid material and the Fresnel equation to describe light transportation between turbid materials of different real refractive indices.

The RT theory defines an absorption coefficient $\mu_a$, scattering coefficient $\mu_s$ and a scattering phase function p(s, s') as the optical parameters characterizing a turbid material, where s and s' are unit vectors representing the light propagation directions before and after a scattering event. To form a boundary-value problem describing light-material interaction, the RT theory has to be supplemented by proper boundary conditions. Reasonable boundary conditions can be formulated with the Fresnel equation in which the light transportation through an interface between two neighboring materials with mismatched real refractive indices n is treated as transverse electromagnetic wavefields. Furthermore, a Henyey-Greenstein (HG) function p(cos α) has been widely used to represent the scattering phase function in turbid materials, where α is the angle between s and s' directions and cos α=s·s'. The form of the HG function is fully determined by a single parameter g, where g is called as the anisotropy factor and defined as the mean value of cos α, i.e., g=<cos α>. With the HG function p(cos α) as the scattering phase function, optical characterization of a turbid sample within the framework of the RT theory and Fresnel equation is reduced to the determination of four optical parameters: $\mu_a$, $\mu_s$, g and n. In general, spectrophotometric characterization of a turbid material is accomplished by determining these parameters as functions of wavelength in the spectrum of interest, which requires accurate measurement of optical signals from the turbid material sample and accurate calculation of these signals based on the RT theory and Fresnel equation.

In existing spectrophotometers, an incident light intensity signal $I_0$ and a collimated transmitted light intensity signal $I_c$ are measured from a sample with photodetectors. A collimated transmittance signal defined as $T_c=I_c/I_0$ is obtained and used to determine the sample's absorbance A and/or attenuation coefficient $\mu_t$ as a function of wavelength based on the Beer's law (also called as the Beer-Lambert's law). The Beer's law can be derived from RT theory if the scattered light from the sample is not present or can be neglected in the detected signal $I_c$. The Beer's law states that the collimated transmittance $T_c$ is related to an attenuation coefficient $\mu_t$ as $T_c=e^{-\mu_t D}$, where $\mu_t=\mu_a+\mu_s$ is the sum of the absorption coefficient $\mu_a$ and scattering coefficient $\mu_s$ and D is the sample thickness along the transmitted light direction. This allows the determination of the absorbance from $A=-\log_{10}(T_c)$ or the attenuation coefficient from $$\mu_t = -\frac{2.30}{D}\log_{10}(T_c)$$

as functions of wavelength λ in the spectrum of interest. We note here that the reflection loss of the light beams at the interfaces between the air and sample holder and between the sample holder and sample is neglected in the definition of $T_c$.

Characterization of a sample in existing spectrophotometers with either A(λ) or $\mu_t(\lambda)$ is accomplished with a monochromatic incident beam of adjustable wavelength and single photodetectors for signal measurement in the spectrum of interest. Spectrophotometric characterization can also be accomplished with a broadband incident light beam in the spectrum of interest and appropriate spectral dispersive devices combined with imaging photodetectors for signal measurement. Here, single photodetectors refer to those light detectors such as photodiodes or photomultipliers with one detecting element and one output signal, and the output signal is related to the total light intensity over the area of the detecting element. Imaging photodetectors refer to those light detectors with multiple detecting elements and multiple signal outputs, and each output signal is related to the light intensity over the area of a specific detecting element. Examples of imaging photodetectors include linear array photodetectors and charge-coupled devices.

It is clear from the Beer's law that either A or $\mu_t$ provides only the information on how much light is attenuated in the material but not on the pathways of light attenuation since attenuation can be caused by absorption ($\mu_t$ is due $\mu_a$) or scattering ($\mu_t$ is due to $\mu_s$). Furthermore, the existing spectrophotometers have no capability to distinguish samples of same $\mu_a$ and $\mu_s$ but exhibiting different characteristics of light scattering (forward scattering, side scattering and backscattering). As an extreme example, both milk and ink attenuate light strongly with the former mainly through light scattering (so it appears white with $\mu_t \approx \mu_s$) while the latter mainly through light absorption (so it appears dark with $\mu_t \approx \mu_a$). Another example is the investigation of certain paints with strong light backscattering capability which are preferred for making road signs easier to be seen by drivers of automobiles with headlights illuminating the signs. Yet, another example is to distinguish different biological cells without the need to stain them with fluorescence dyes by the spectrophotometric determination of all the optical parameters of the cell suspension samples. These examples illustrate the needs for a new type of spectrophotometers to accurately characterize turbid materials with the optical parameters of $\mu_a$, $\mu_s$, g and n.

Determination of the above optical parameters requires accurate measurement of light signals scattered out of a turbid material sample in addition to the collimated transmitted light signal followed by calculation of these signals on the basis of an accurate optical model such as the RT theory and Fresnel equation. Several methods have been developed to determine some of the four optical parameters of $\mu_a$, $\mu_s$, g and n. None of these methods, however, can be used to determine $\mu_a$, $\mu_s$, g and n in one instrument. Recently, an integrating sphere based method has been developed as a primary method to determine $\mu_a$, $\mu_s$, g and n as functions of wavelength. In this method, a device of integrating sphere is used to measure the diffuse reflectance signal $R_d$ and diffuse transmittance signal $T_d$, a spatial filtering device is used to measure the collimated transmittance signal $T_c$ and a prism based device is used to determine the coherent reflectance signal $R_c$ as a function of incident angle θ of a monochromatic light beam. The real refractive index n is obtained by fitting the calculated values of $R_c(\theta)$ using the Fresnel equation to the measured values of $R_c(\theta)$. This is followed by the determination of the optical parameters of $\mu_a$, $\mu_s$ and g from the measured signals of $T_c$, $T_d$ and $R_d$ using the Beer's law and a Monte Carlo simulation method within the framework of RT theory.

Despite its ability to determine the optical parameters of $\mu_a$, $\mu_s$, g and n, the integrating sphere based method requires the use of three optical devices as discussed in the forgoing. The experimental procedures of the integrating sphere based method require that the turbid material be made into slab samples of different thickness (or in sample holders of different thickness) and moved between the three devices. Therefore, this method is time consuming, prone to error and of limited usefulness to industrial and/or biomedical applications.

In view of the forgoing, it would be an advance in the art to provide method and apparatus for measuring optical signals in one instrument from a turbid material sample without the need for an integrating sphere and prism and for determining the optical parameters of $\mu_a$, $\mu_s$, g and n as functions of wavelength. It would also be an advance in the art to provide the methods and apparatus for accurate and rapid measurement of the optical signals and determination of the optical parameters.

BRIEF SUMMARY OF THE INVENTION

According to embodiments of the present invention, methods are provided for spectrophotometric characterization of a turbid material through determination of optical parameters of an absorption coefficient $\mu_a$, a scattering coefficient $\mu_s$, an isotropy factor g and a real refractive index n of a turbid material sample as functions of wavelength. An incident light beam from a light source illuminates the sample which is homogeneous meaning that the optical parameters of $\mu_a$, $\mu_s$, g and n remain as constants inside the sample. The following optical signals are acquired as functions of wavelength from the sample using multiple photodetectors with no contact with the sample: coherent reflectance signal $R_c$, collimated transmittance signal $T_c$, diffuse reflectance signal $R_d$, diffuse transmittance signal $T_d$.

The spatial locations and orientations of the single and linear array photodetectors relative to the sample are accurately simulated in an optical model on the basis of RT theory and Fresnel equation. The simulation allows accurate analysis of light transportation through the sample impinged by the incident light and calculation of optical signals as a result of light being collected by the photodetectors. The calculated signals are obtained in the simulations with the initial or updated values of the optical parameters of $\mu_a$, $\mu_s$, g and n. The calculated signals are compared to the measured signals to obtain relative errors and the simulations are iterated with updated parameters until each error is reduced to a pre-determined minimum value, which is typically the corresponding experimental error. After the simulation is terminated, the last updated parameter values are saved as the optimized values of $\mu_a$, $\mu_s$, g and n at the wavelength of measured signals. This process is repeated at all wavelengths of the measure signals to obtain $\mu_a$, $\mu_s$, g and n of the turbid material sample as functions of wavelength in the spectrum of interest.

In some embodiments of the present invention, an appropriate monochromater is used with a broadband light source to produce a monochromatic incident beam of adjustable wavelength for spectrophotometric measurement of optical signals with single and linear array photodetectors. The broadband light source can be an incoherent lamp source and the monochromater contains a dispersive device such as a prism, an interference filter or a grating. In other embodiments of the present invention, a monochromatic incident light beam of adjustable wavelength is obtained by switching among multiple narrowband sources such as lasers or light emitting diodes.

In some embodiments of the present invention, the multiple photodetectors comprise single and linear array photodetectors at fixed locations to measure optical signals from the turbid material sample excited by a monochromatic incident light beam. A linear array photodetector is a monolithic light detector containing two to more detecting elements arranged side by side to detect the light intensity distributed at multiple spatial locations or multiple angles relative to the incident light beam. In other embodiments of the present invention, the multiple photodetectors comprise two or more single photodetectors at fixed or adjustable spatial locations to measure the optical signals from the sample illuminated by a monochromatic incident light beam.

In some embodiment of the present invention, a broadband incident light beam is used to illuminate the turbid material sample. Appropriate spectral detectors are used with dispersive devices and imaging photodetectors for spectrophotometric measurement of optical signals at multiple spatial locations or multiple angles relative to the incident light beam.

In some embodiments of the present invention, determining the absorption coefficients $\mu_a$, scattering coefficient $\mu_s$, anisotropy factor g and real refractive index n of the sample from the measured optical signals is based on an optical model of Monte Carlo simulation. In other embodiments of the present invention, determining $\mu_a$, $\mu_s$, g and n of the sample from the measured optical signals is based on the numerical solution of the boundary-value problem consisting of the RT equation and boundary conditions based on the Fresnel equation.

BRIEF DESCRIPTION OF THE DRAWINGS

In order to better appreciate the differences of the new spectrophotometer of the present invention in comparison to the existing spectrophotometers, a more detailed description of the present invention briefly discussed above will be provided by reference to a specific embodiment thereof which is illustrated in the appended drawings. Understanding that the present invention may, however, be embodied in many different forms and should not be construed as limited to the embodiments set forth herein. Rather, the embodiments described in the appended drawings are provided so that this disclosure will be thorough and complete, and will fully convey the scope of the present invention to those skilled in the art.

DETAILED DESCRIPTION OF THE INVENTION

Figure 1:
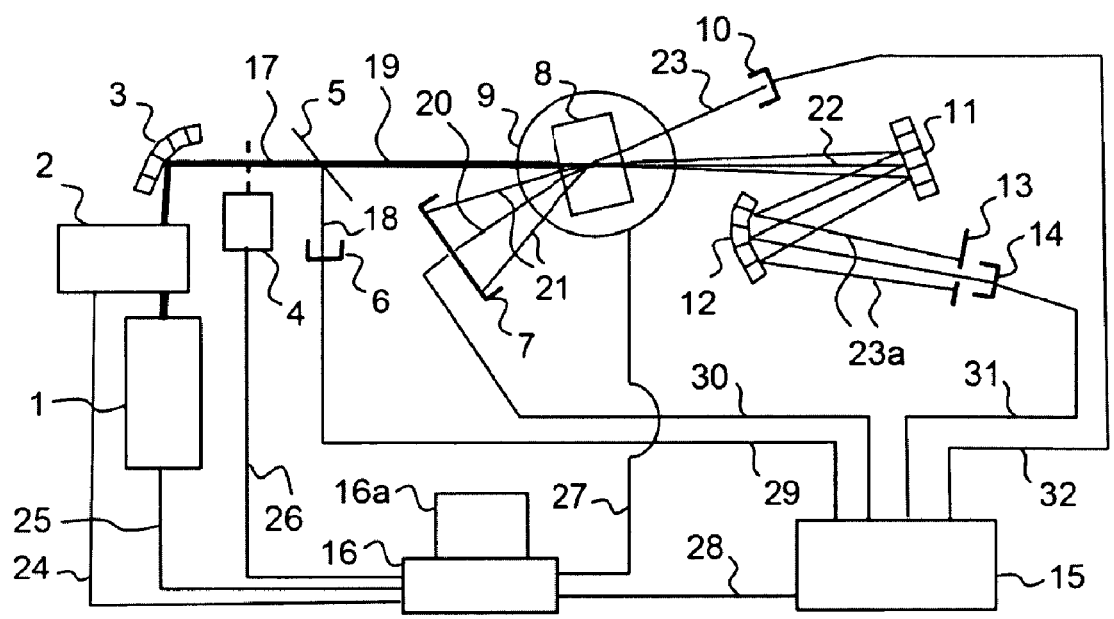
FIG. 1 is a schematic diagram of an embodiment of the new spectrophotometer in accordance with the present invention.

Reference will now be made to the appended drawings. Like numbers refer to like elements throughout. In the appended drawings, the thickness of certain lines, layers, components, elements or features may be exaggerated for clarity. The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of those skilled in the art to which the present invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The present invention is described below with reference to block diagrams and/or flow chart illustrations of methods, apparatus and/or computer program products according to embodiments of the present invention. It is understood that each block of the block diagrams and/or flow chart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flow chart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flow chart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flow chart block or blocks.

Accordingly, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

Reference will next be made to FIG. 1, which is a schematic diagram of an embodiment of the present invention.

The embodiment as illustrated in FIG. 1 preferably includes components for carrying out the functions of detecting optical signals as functions of wavelength of an monochromatic incident light beam: a coherent reflectance signal $R_c$, a collimated transmittance signal $T_c$, a diffuse reflectance signal $R_d$ and a diffuse transmittance signal $T_d$.

A broadband light source 1 controlled by a computer 16 through an electric wire 25 produces a focused light beam on the input slit of an appropriate monochromater 2, which utilizes a dispersive device such as a grating to produce multiple monochromatic beams propagating along different directions in accordance with their wavelengths. Inside the monochromater 2, the beams from the dispersive device are focused at its output slit which selects one monochromatic beam as the output.

The wavelength $\lambda$ of the output beam can be varied in the spectrum of interest by rotating the dispersive device inside the monochromater 2 in relation to the output slit with an electronic control signal transmitted through an electric wire 24. It is to be understood that any appropriate wavelengths of light can be used and that the term "light" is intended to mean any appropriate wavelengths of electromagnetic radiation and all such wavelengths, including all devices may now be available or which may be available in the future to generate such radiation, are all intended to fall within the scope of the present invention. In one embodiment, $\lambda$ of the output beam from the monochromater 2 in the spectrum of interest can be varied in a range from 200 nm to 1000 nm. In another embodiment, $\lambda$ in the spectrum of interest can be varied in a range from 400 nm to 3000 nm.

A curved mirror 3 collimates and passes the output light beam of the monochromater 2 through a light modulator 4 to obtain a beam 17 propagating toward the beam splitter 5. One embodiment of the beam modulator 4 rotates a metal blade with multiple open slots using an electric motor in the passing beam such that the intensity of the beam 17 becomes zero with the blade blocking the beam and remains the same as the beam from the curved mirror 3 with an open slot in the beam. In another embodiment of the beam modulator 4, an acoustic-optical modulator can be used to rotate the direction of the beam 17 so that its intensity after a beam blocker can be modulated. The beam modulator 4 is controlled by the computer 16 through an electric wire 26 and the frequency of modulation is sent to the computer 16 for signal demodulation. Those skilled in the art appreciate that the intensity modulation of the beam 17 allows the detection of the weak signals related to the scattered light with sufficient signal-to-noise ratios when the signals are acquired in a data acquisition unit 15 and demodulated in the computer 16.

The beam splitter 5 separates the beam 17 into two components: a transmitted light beam 19 that is incident on the sample assembly 8 and a reflected light beam 18 which is detected by the photodetector 6. The signal from the photodetector 6 is sent to the data acquisition unit 15, which is linearly proportional to the intensity of incident light beam 19 and used for signal normalization in measuring the optical signals of $R_c$, $T_c$, $R_d$ and $T_d$.

The incident light beam 19 arrives at a sample assembly 8 consisting of a turbid material sample and a sample holder, and illuminates the sample assembly 8 such that the scattered light signals are present in both of the reflected directions and transmitted directions. The coherently reflected light beam 20 is due to coherent reflection of the incident light with a reflection angle equal to the incident angle according to the reflection law. The linear array photodetector 7 contains multiple detecting elements and signals produced by the detecting elements are sent sequentially to the data acquisition unit 15 through an electric wire 30. The detecting element of the linear array detector 7 which outputs the largest signal among all the detecting elements represents the coherent reflection signal while the other detecting elements represent the diffuse reflection signals.

The coherent reflection signal is normalized by the signal from the photodetector 6 in the data acquisition unit 15 for obtaining the coherent reflectance $R_c$ at the incident angle $\theta$ and wavelength $\lambda$ of the incident light beam 19. The measured optical signal of $R_c(\theta)$ needs to be acquired at two or more values of $\theta$ by rotating the sample assembly 8. Acquiring $R_c$ at multiple $\theta$ increases the accuracy of the real refractive index of the turbid material sample determined from $R_c(\theta)$ but needs longer data acquisition time. In one embodiment of the present invention, the number of $\theta$ values can range between 2 and 10. In another embodiment of the present invention, the number of $\theta$ values can range between 5 and 100.

The signals presented by the other detecting elements of the linear array photodetector 7 are related to the diffusely reflected light beams 21, which are summed in the data acquisition unit 15 to obtain a diffuse reflection signal. The diffuse reflection signal is normalized by the signal from the photodetector 6 for obtaining the diffuse reflectance $R_d$ at $\lambda$ of the incident light beam 19 in the spectrum of interest.

The transmitted light beam 22 propagates along the same direction of the incident beam and arrives at a photodetector 14 after reflection at a flat mirror 11 and a curved mirror 12. A slit 13 is positioned to allow the passage of the transmitted beam 22 after its reflection at the flat mirror 11 and focused reflection at the curved mirror 12. The slit 13, however, blocks the forwardly scattered light beams 23a after the focused reflection at the curved mirror 12 to prevent their detection by the photodetector 14. The signal from the photodetector 14 is acquired by the data acquisition unit 15 through an electric wire 31 for obtaining the measured value of the collimated transmittance $T_c$ at $\lambda$ of the incident light beam 19 after normalization by the signal from the photodetector 6.

The width of the slit 13 affects the accuracy of the collimated transmittance measurement which is related to the intensity of the transmitted beam 22. The signal-to-noise ratio of $T_c$ will be small if the slit is very narrow since some of the transmitted beam 22 as the signal from the photodetector 14 is blocked at 13, whereas the accuracy of $T_c$ will decrease if the slit is very wide since some of the forwardly scattered light beams 23a will reach the photodetector 14. In one embodiment, the slit width is set to values between 0.02 mm and 2.0 mm. In another embodiment, the slit width is set to values between 0.1 mm and 10.0 mm. The forwardly scattered light beam 23 deviates from the direction of the incident light beam at a large angle and arrives at the photodetector 10. The signal from the photodetector 10 is acquired by the data acquisition unit 15 through an electric wire 32 for measurement of the diffuse transmittance $T_d$ at $\lambda$ of the incident light beam 19 after normalization by the signal from the photodetector 6.

The data acquisition unit 15 is used to acquire and digitize the modulated light signals from the photodetector 6, linear array photodetector 7, photodetector 10 and photodetector 14. The data acquisition unit 15 is capable of gain control, acquisition and digitization of individual signals from each of the multiple detecting elements of the linear array photodetector 7 sequentially. The signals acquired and digitized by the data acquisition unit 15 are sent through the electric wire 28 to the data processing program stored in the computer 16 to demodulate the signals and produce the measured optical signals of $R_c$, $T_c$, $R_d$ and $T_d$. The computer 16 has a display 16a for users to select, enter and display various input and output control parameters of the spectrophotometer in accordance to the present invention. The computer 16 is also programmed to adjust the wavelength λ of the incident beam 19 by controlling the monochromater 2 through the electric wire 24 and the intensity of the incident light beam 19 by controlling the broadband light source 1 through wire 25. Furthermore, the computer 16 is programmed to rotate the sample assembly table 9 so that the incident angle of the incident light beam 19 can be varied in the desired range.

Figure 2:
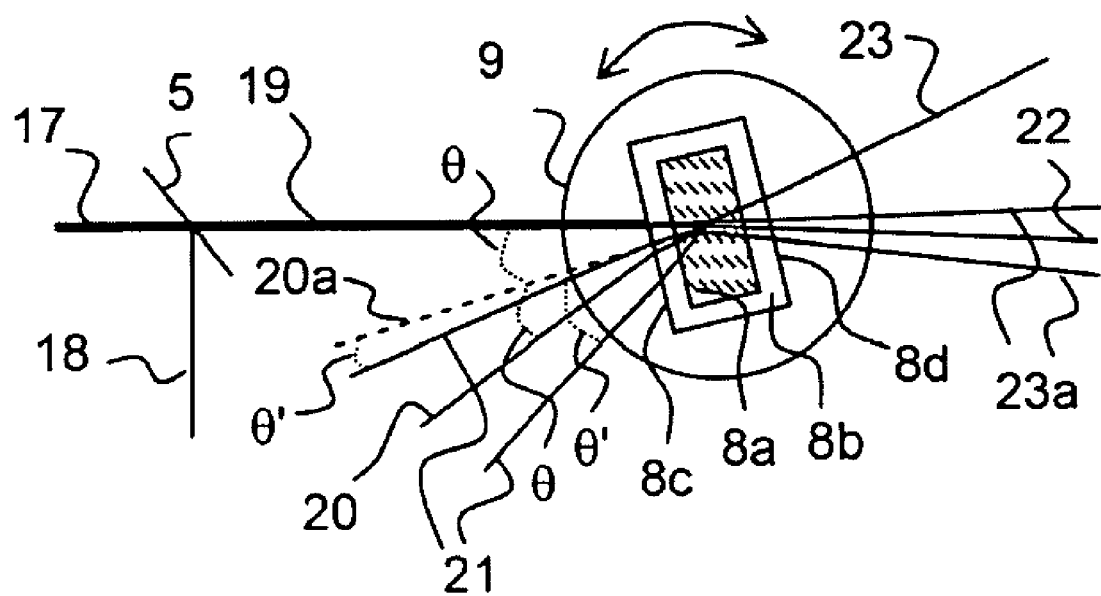
FIG. 2 is a schematic diagram of various optical signals from a turbid material sample in relation to the incident light beam in an embodiment of the present invention.

Reference will next be made to the detailed view of the light beams and sample assembly in FIG. 2. The turbid material sample 8a is placed in a sample holder 8b. For solid or rigid turbid samples, the sample holder may not be needed and the sample assembly consists of only the turbid material sample. The sample assembly has a front surface 8c facing the incident light beam and rear surface 8d that are often parallel to each other. Those skilled in the art should appreciate that intensity of the reflected light is dependent on the reflection angle relative to the normal direction 20a of the front surface 8c. The coherently reflected light beam 20 is reflected at a reflection angle θ that is equal to the incident angle θ of the incident light beam 19 in accordance to the reflection law. The diffusely reflected light beams 21, however, propagate in directions along the angle θ' that are not equal to the incident angle θ and usually have intensities less than that of the coherently reflected light beam 20.

The sample assembly table 9 contains a stepping motor to vary the incident angle θ by rotating the sample assembly 8. This allows the measurement of the intensity of coherently reflected light beam 20 at multiple values of the incident angle θ and obtaining the coherent reflectance $R_c$ as a function of θ. The dependence of $R_c$ on θ is used to determine the real refractive index n of the turbid material sample 8a on the basis of the Fresnel equation. The measurement of the intensity of transmitted light beam 22 and the thickness of the turbid material sample 8a along the transmitted light direction allows obtaining collimated transmittance $T_c$, which can be used to determine the attenuation coefficient $\mu_t$ on the basis of the Beer's law. The use of the curved mirror 12 and the slit 13 improve the accuracy of the $\mu_t$ determined from $T_c$ by removal or significant reduction of the forwardly scattered light beam 23a from the signals detected by the photodetector 14.

The intensity detection of the diffusely reflected light beams 21 and the forwardly scattered light beam 23 by the linear array photodetector 7 and photodetector 10, respectively, allows obtaining of the measured optical signals $R_d$ and $T_d$. These two optical signals will be used in the optical model based on the RT theory to determine the optical parameters of the scattering albedo a=$\mu_s/\mu_t$ and g. The parameters of $\mu_t$ and a can be converted to $\mu_a$ and $\mu_s$ to obtain the optical parameters of $\mu_a$, $\mu_s$ g and n in the spectrum of interest.

Figure 3:
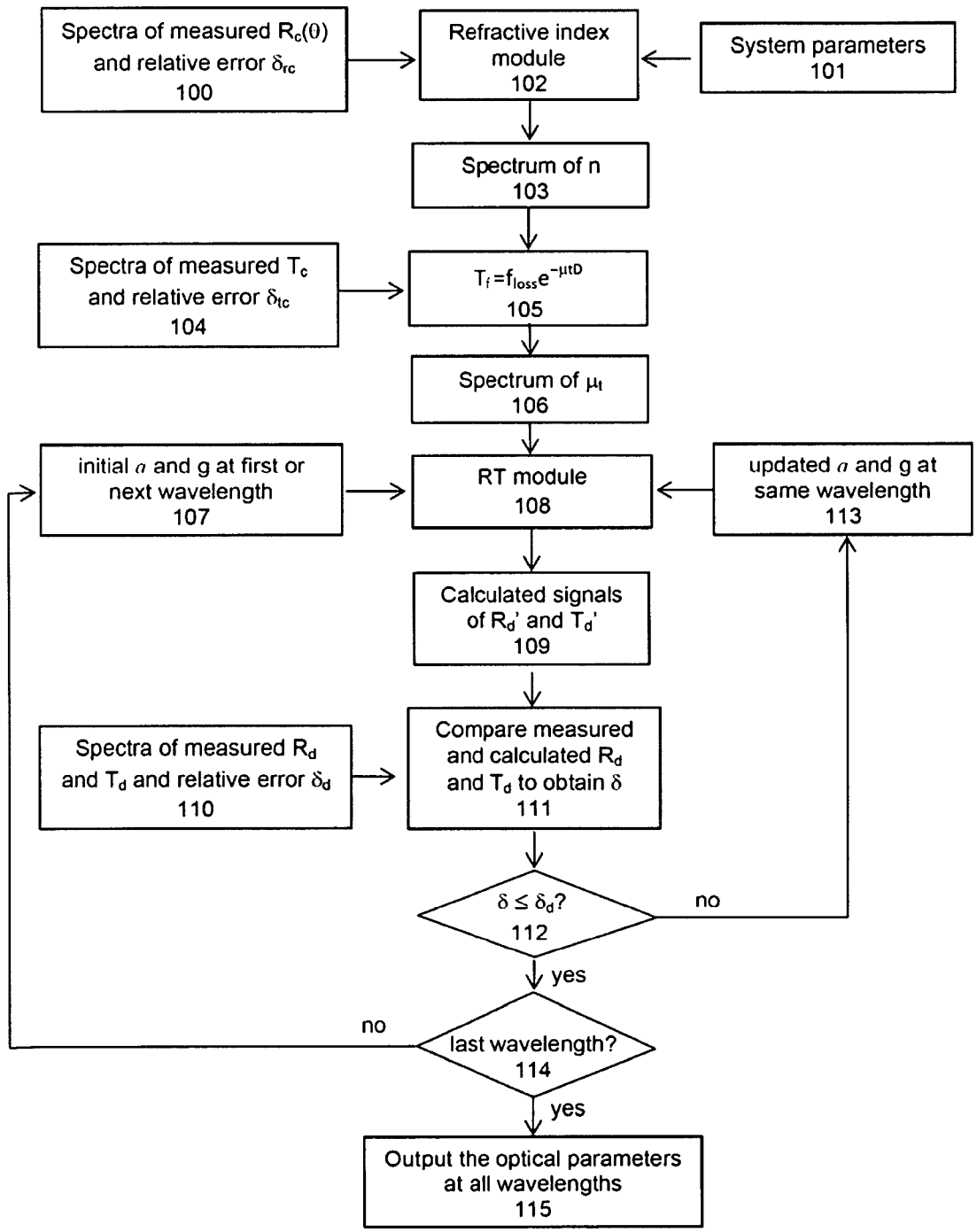
FIG. 3 is a flow-chart diagram of the method representing an embodiment of the present invention for determination of optical parameters of a turbid material sample from the measured optical signals acquired at wavelengths within the spectrum of interest.

Reference will now be made to FIG. 3 which is a flow chart diagram of the method representing an embodiment of the present invention for determination of the optical parameters of a turbid material sample from the measured optical signals. The method starts with an input block 100 providing the measured coherent reflectance signal $R_c(\theta)$ at each wavelength λ in the spectrum of interest. The input block 100 also provides the spectrum of the relative errors $\delta_{rc}$, which is defined as the mean, relative error of $R_c$ measurement averaged over all incident angles of the incident light beam 19. Another input block 101 provides the system parameters that include the diameter of the incident light beam 19, the dimensions of the sample 8a, the dimension and the real refractive index of the sample holder 8b, the location and orientation of the photodetectors relative to the sample holder 8b. The refractive index module in block 102 will be used to determine the real refractive index n of the turbid material sample at each wavelength λ in the spectrum of interest from the measured signal of $R_c(\theta)$. The output of the block 102 is saved as the spectrum of real refractive index for the turbid material sample in block 103.

The Beer's law module in block 105 is used to calculate the attenuation coefficient $\mu_t$ as a function of λ in the spectrum of interest from $T_c$ and relative errors $\delta_{tc}$, which is defined as the mean relative error of $T_c$ measurement, in block 104 and spectrum of n in block 103. The Beer's law states that $T_c = f_{loss} e^{-\mu_t D}$, where $f_{loss}$ is a numerical factor less than 1 due to the reflection loss of the incident and transmitted beams at the air-holder and holder-sample interfaces and D is the pathlength of the incident beam 19 through the sample provided in block 101. The factor $f_{loss}$ can be calculated from the incident angle θ of the light beam 19 and the real refractive indices of the sample holder and sample according to the Fresnel equation and allows the calculation of $\mu_t$ as $$\mu_t = -\frac{2.30}{D}\log_{10}\left(\frac{T_c}{f_{loss}}\right).$$

The attenuation coefficient $\mu_t$ at a wavelength λ can also be obtained by calculation of the slope of the straight line in a plot of $\log_{10}(T_c)$ versus D with $T_c$ measured at multiple D. In one embodiment of the present invention, D can be varied by changing the sample thickness between the front surface 8c and rear surface 8d. In another embodiment of the present invention, D can be varied with a constant sample thickness by changing the incident angle θ of the incident light beam. Calculation of $\mu_t$ from the slope of the $\log_{10}(T_c)$ versus D plot requires no knowledge of $f_{loss}$ and typically is more accurate than that obtained from the Beer's law with just one value of D. The results of the Beer's law module in block 105 is saved as the spectrum of $\mu_t$ for the turbid material sample in block 106

The RT module in block 108 produces the calculated optical signals of $R_d{'}$ and $T_d{'}$ which can be compared to the measured diffuse reflectance $R_d$ and diffuse transmittance $T_d$. The initial values of the optical parameters of scattering albedo a defined as a=$\mu_s/\mu_t$ and g are first set in block 107 at a selected wavelength in the spectrum of interest. The range of either a or g is between 0 and 1 and the initial values can be set to any numbers between 0 and 1 and are typically set to the middle of the range at 0.5. The output of the RT module in block 108 is saved as the $R_d{'}$ and $T_d{'}$ in block 109, which are used in block 111 to calculate their difference from the measured values of $R_d$ and $T_d$ provided by block 110. The block 110 also provides the relative errors $\delta_d$ which is defined as the mean relative error of $R_d$ and $T_d$ measurements.

The difference between the measured and calculated signals of diffuse reflectance and diffuse transmittance is quantitatively expressed as an error function δ in block 111. The value of δ is used to decide if an iterated process of calculating $R_d{'}$ and $T_d{'}$ in the RT module in block 108 to be continued or not. One embodiment of the error function δ in the present invention is to calculate the mean-root-square of the relative difference between the calculated and measured values of diffuse reflectance and diffuse transmittance as $$\delta = \sqrt{\left|\frac{R_d - R'_d}{R_d}\right|^2 + \left|\frac{T_d - T'_d}{T_d}\right|^2}.$$

Another embodiment of the error function δ in the present invention is to calculate the sum of the absolute values of the relative difference between the calculated and measured values of diffuse reflectance and diffuse transmittance as $$\delta = \left|\frac{R_d - R'_d}{R_d}\right| + \left|\frac{T_d - T'_d}{T_d}\right|.$$

If the comparison in block 112 produces a negative result, the optical parameters of a and g will be adjusted from their last values to updated values in block 113 according to an inverse algorithm. With the updated optical parameters, the RT module will obtain the calculated values of $R_d$ and $T_d$ again for the next comparison in block 112. One embodiment of the inverse algorithm is to change the values of the optical parameters based on the comparison of $R_d'$ and $T_d'$ relative to $R_d$ and $T_d$: if $R_d'+T_d'<R_d+T_d$, then decrease a from its last value, otherwise increase a; if $$\frac{T'_d}{R'_d} < \frac{T_d}{R_d}$$

then increase g from its last value, otherwise decrease g. Another embodiment of the inverse algorithm is to change the values of a and g based on the direction of change between the values of δ from the last two consecutive iterations and the ratios of the change in δ to the sizes of the changes in a and g, which is known as the gradient based algorithm to those skilled in the art.

If the comparison in block 112 produces a positive result, the method for determination of optical parameters will check if the wavelength at which the optical parameters are optimized is the last one in the spectrum of interest in block 114. If the answer to the question in block 114 is negative, the algorithm flows back to block 107 to set initial values of a and g at the next wavelength and repeat calculation of $R_d'$ and $T_d'$ in block 108. If the answer to the question in block 114 is positive, the optimized optical parameters of $\mu_t$, g and n will be converted to $\mu_a$, $\mu_s$, g and n at all wavelengths in the spectrum of interest in the block 115 and then saved as the output data.

Figure 4:
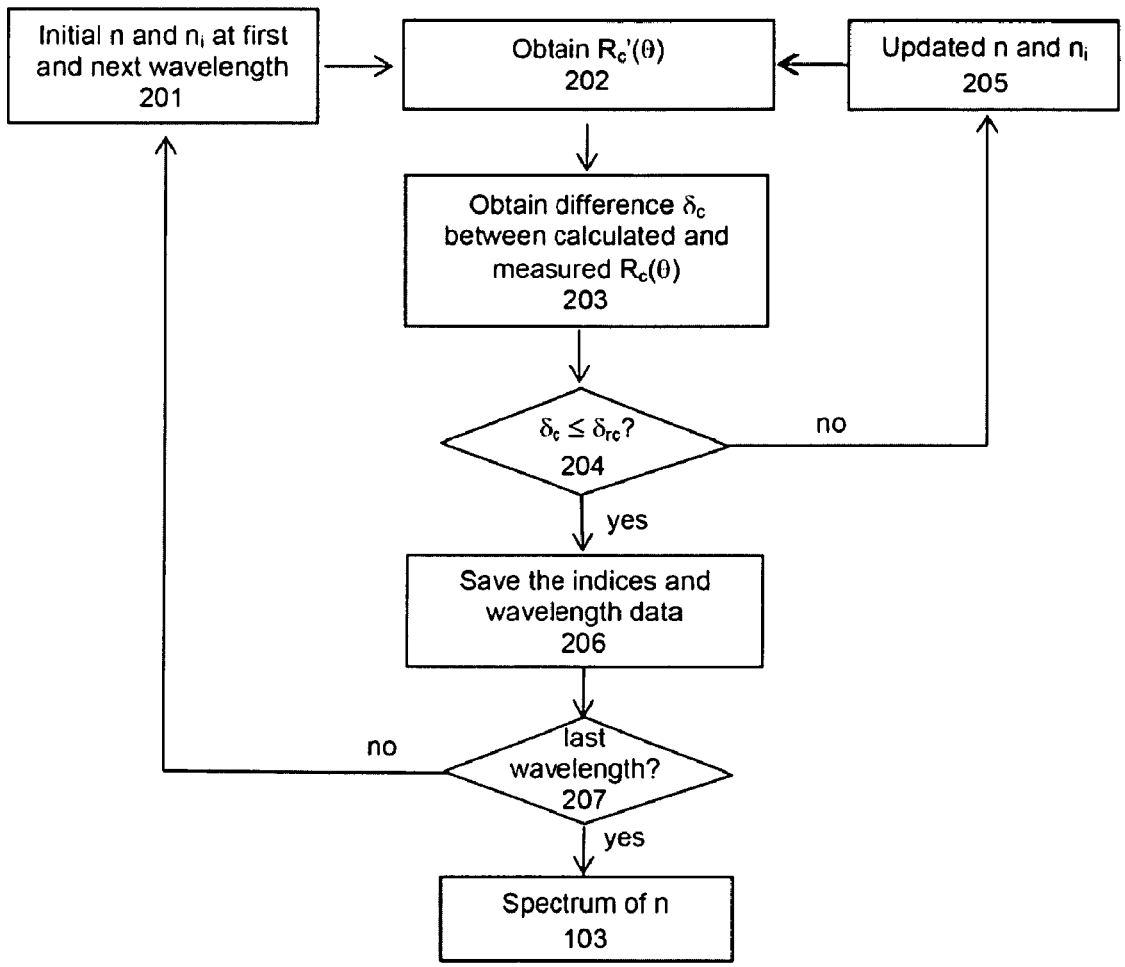
FIG. 4 is a flow-chart diagram of the method representing an embodiment of the present invention for determination of the real refractive index spectrum of a turbid material sample based on the Fresnel equation.

Reference will now be made to FIG. 4 on the details of the refractive index module referred to in block 102 of FIG. 3 to determine the real refractive index n of a turbid material sample in the spectrum of interest based on the Fresnel equation. The method starts by calculating the coherence reflectance as a function of the incident angle θ as $R_c'(\theta)$ in block 202 with the initial values of n and $n_i$ of the turbid material sample provided by the block 201, where the parameter $n_i$ is the imaginary refractive index of the sample. The calculated value of the coherence reflectance $R_c'(\theta)$ is obtained in block 202 from the following Fresnel equation for an unpolarized incident light beam $$R'_c(\theta) = \frac{1}{2}\left|\frac{n_0\cos\theta - \sqrt{(n+in_i)^2 - n_0^2\sin^2\theta}}{n_0\cos\theta + \sqrt{(n+in_i)^2 - n_0^2\sin^2\theta}}\right|^2 +$$
$$\frac{1}{2}\left|\frac{(n+in_i)^2\cos\theta - n_0\sqrt{(n+in_i)^2 - n_0^2\sin^2\theta}}{(n+in_i)^2\cos\theta + n_0\sqrt{(n+in_i)^2 - n_0^2\sin^2\theta}}\right|^2$$

where $n_0$ is the real refractive index of the sample holder 8b in contact with the turbid material sample and $i=\sqrt{-1}$. The incident angle θ takes the same values as those employed to measure the coherent reflectance signal $R_c(\theta)$ by rotating the sample assembly 8 and the number of the θ values needs to be two or larger.

The block 203 compares the difference between the measured and calculated coherent reflectances by obtaining an error function $\delta_c$ defined in the following $$\delta_c = \sqrt{\sum_\theta \left|\frac{R_c(\theta) - R'_c(\theta)}{R_c(\theta)}\right|^2},$$

where the sum is over all values of θ. The error function $\delta_c$ is compared to the experimental error $\delta_{rc}$ in measurement of $R_c(\theta)$ in block 204. If the comparison in block 204 produces a negative result, the refractive indices n and $n_i$ of the turbid material sample 8a will be adjusted from their last values to updated values in block 205 and the process of calculating and comparing the coherent reflectances will be repeated. If the comparison in block 204 produces a positive result, the refractive indices of n and $n_i$ at the selected wavelength will be saved in block 206. The next step of the method is to check if the selected wavelength is the last wavelength in the spectrum of interest in block 207. If the answer is negative, the process of determining the real refractive index will start from block 201 for the next wavelength until the check in block 207 receives a positive answer. At this point, the spectrum of the real refractive index n for the turbid material sample will be sent to and saved in block 103 as shown in FIG. 3.

The value of the imaginary refractive index $n_i$ depends on the absorption coefficient $\mu_a$ and scattering coefficient $\mu_s$ of the sample and thus relates to the attenuation of the incident beam inside the sample. Since the $\mu_a$ and $\mu_a$ are determined from other measured signals of $R_d$, $T_c$ and $T_d$ in the present invention, it is well understood that to those in the art that $n_i$ is of little use for characterizing a turbid material. Therefore, the imaginary refractive index $n_i$ is only used in the refractive index module as an fitting parameter instead of an optical parameter.

Figure 5:
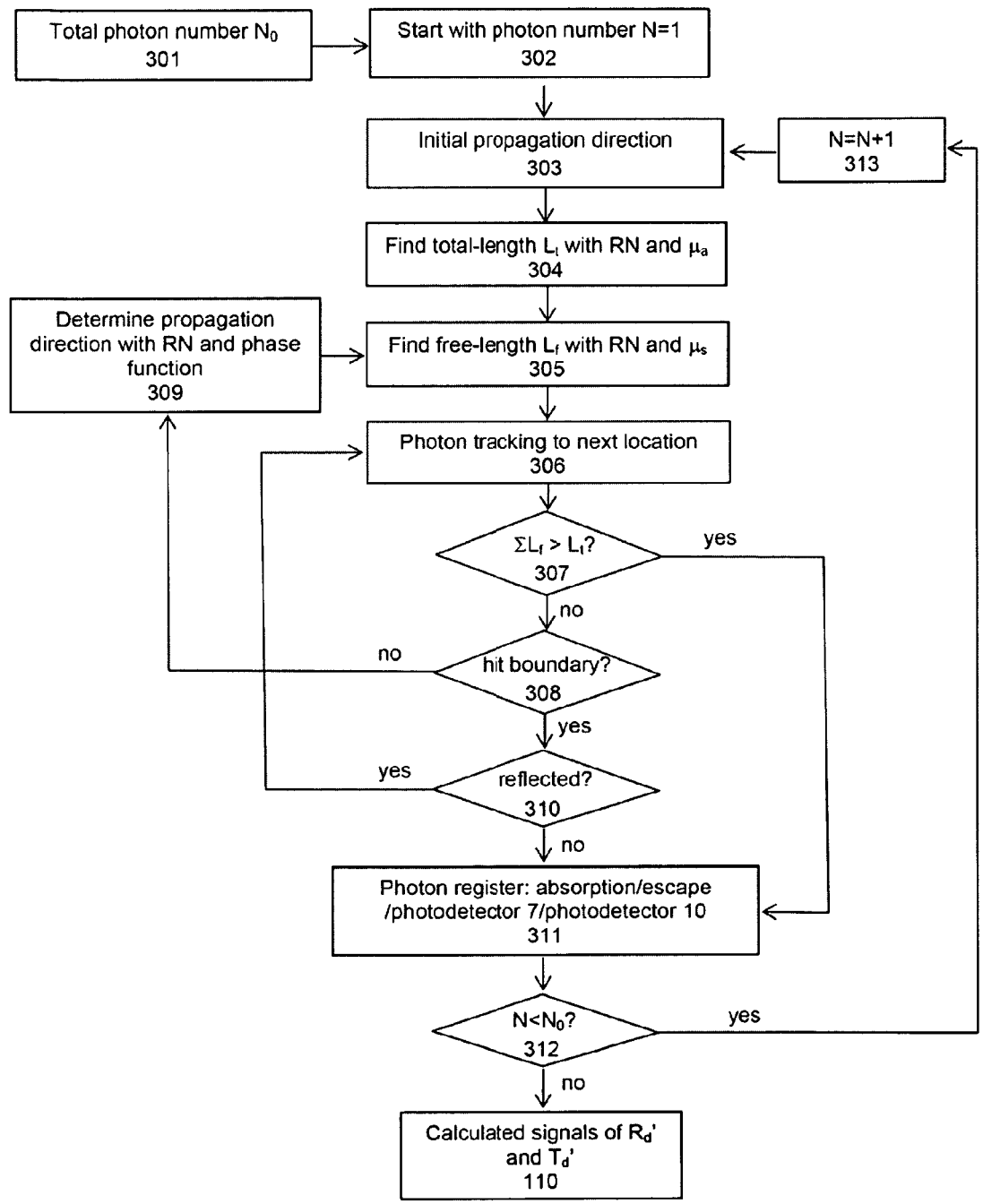
FIG. 5 is a flow-chart diagram of the method representing an embodiment of the present invention for obtaining calculated optical signals based on the Monte Carlo simulation.

Reference will now be made to FIG. 5 on the details of the RT module referred to in 109 of FIG. 3 for obtaining calculated values of diffuse reflectance $R_d'$ and diffuse transmittance $T_d'$ in the spectrum of interest. The RT module produces $R_d'$ and $T_d'$ by solving a boundary-value problem described by the following steady-state RT equation $$s\cdot\nabla L(r,s) = -(\mu_a+\mu_s)L(r,s)+\mu_s\int_{4\pi}p(s,s')L(r,s')d\Omega'$$

In combination with the Fresnel equation discussed earlier in relation to FIG. 4 as the boundary condition. In the above RT equation, s and s' are unit vectors representing the light propagation directions, ∇ is a gradient operator, r is a location vector, L(r, s) is the light radiance at r location along the s direction, dΩ' is a solid angle element along the s' direction in 3-dimensional space and the angular integral is to be integrated over all possible solid angles of $4\pi$ steradian. One embodiment of the RT module is through Monte Carlo simulations in which the incident light is represented by a statistically large ensemble of photons. Another embodiment of the RT module is to numerically solve the boundary-value problem based on the RT equation and Fresnel equation for obtaining the calculated optical signals of $R_d'$ and $T_d'$.

FIG. 5 presents a flow chart diagram of a Monte Carlo simulation algorithm as a preferred embodiment of the present invention to simulate photon transportation within a turbid material sample and obtain calculated diffuse reflectance $R_d'$ and diffuse transmittance $T_d'$ that can be compared to the measured values of $R_d$ and $T_d$. In a Monte Carlo simulation, the portion of the incident light beam 19 entering the sample assembly 8 is represented by an ensemble of photons with a total number of $N_0$ provided in block 301. Each of the injected photons is individually tracked with stochastic processes inside the sample assembly 8 according to the optical parameters of the sample and the system parameters until all tracked photons exit the sample assembly 8. Those photons collected by the photodetectors are registered in the computer memory and normalized by $N_0$ to produce the calculated signals. The number $N_0$ has to be sufficiently large so that the statistical fluctuations is negligible in the calculated signals based on the stochastic process of photon tracking in a Monte Carlo simulation to ensure the accuracy of the results.

Photon tracking in a Monte Carlo simulation starts with the first photon of sequence number N set to 1 in block 302 and continues by increment of N by 1 until $N > N_0$. Each of the incident photons take the same incident angle $\theta$ as the incident light beam 19 which is used to obtain the initial direction of the photon propagation at the refraction angle $\theta'$ inside the sample 8a in block 303 according to the Snell's law of refraction. A total-length of photon travel $L_t$ for the tracked photon inside the sample 8a is first determined in block 304 by a random number (RN) according to a distribution such that the mean value of $L_t$ averaged over all tracked photons must equal to the inverse of $\mu_a$. Then the free-length of the tracked photon before the next scattering site $L_f$ is determined in block 305 with a RN according to a distribution such that the mean value of $L_f$ averaged over all tracked photons must equal to the inverse of $\mu_s$.

The block 306 is used to calculate location of next scattering site for the tracked photons after receiving the information on $L_f$ provided by block 305 and on the direction of propagation provided by block 303 based on the refraction angle or block 309 based on the scattering phase function. The direction of photon propagation s' after a scattering event is calculated in block 309 with a RN distributed according to the scattering phase function $p(\cos \alpha)$ for the polar angle $\alpha$ relative to the direction s of the tracked photon and another RN distributed uniformly between 0 and $2\pi$ for the azimuthal angle $\phi$. It should be noted here that the dependence of the HG function on $\cos \alpha$, $p(\cos \alpha)$, is fully determined by the value of the anisotropy factor g.

Every time before the tracked photon is allowed to propagate to the next scattering site, its accumulated free-length $\Sigma L_f$ is compared to the total-length $L_t$ in block 307 to examine if it is being absorbed. If the answer is positive, the tracked photon is registered as an absorbed photon in block 311 and tracking of this photon is terminated. If the answer is negative, the tracked photon is next checked in block 308 to see if it hits the boundary of the sample 8a. If the tracked photon hits the boundary, the reflection probability $P_R$ of the photon being reflected back into the sample 8a is calculated as the coherent reflectance through the Fresnel equation. The reflection probability $P_R$ is compared to a RN uniformly distributed between 0 and 1 in block 310. If $RN < P_R$ the tracked photon is injected back into the sample 8a along the reflection direction and complete the current free-length in block 306 until reaching the next scattering site. Otherwise, the tracked photon enters into the sample holder 8b where the photon transportation is tracked as traveling along a straight line until hitting the outer surface of the sample holder 8b. Here we assume that the sample holder is made of material transparent to the incident light in the spectrum of interest with neither absorption nor scattering, but having a real refractive index different from that of the sample in general. The reflection and refraction of the tracked photon at the out surface of the sample holder 8b are treated with exactly the same approach as that used for the surface of the sample 8a.

If the tracked photon exits the sample holder 8b into the ambient air, its location and direction of propagation at the outside surface of the sample holder 8b are obtained to check if it hits the photodetector and register accordingly in block 311. If the photon does not hit any photodetector, it is registered as an escape photon. If the tracked photon hits one of the detecting elements in the photodetector 7, it is registered as a photon contributing to the calculated signal of diffuse reflectance $R_d'$. In comparison, if the tracked photon hits the photodetector 10, it is registered as a photon contributing to the calculated signal of diffuse transmittance $T_d'$. After the photon registration in block 311, the sequence number of the tracked photon N is checked against the total number $N_0$ of photons to be tracked. If $N < N_0$, then N is increased by 1 in block 313 and the photon tracking is executed with the next photon. Otherwise, the photon tracking will be completed and the calculated optical signals of $R_d'$ and $T_d'$ will be saved as output in block 110, where $R_d'$ is defined as the ratio of the total number of photons detected by photodetector 7 to $N_0$ and $T_d'$ is defined as the ratio of the total number of photons detected by photodetector 10 to $N_0$.

Figure 6:
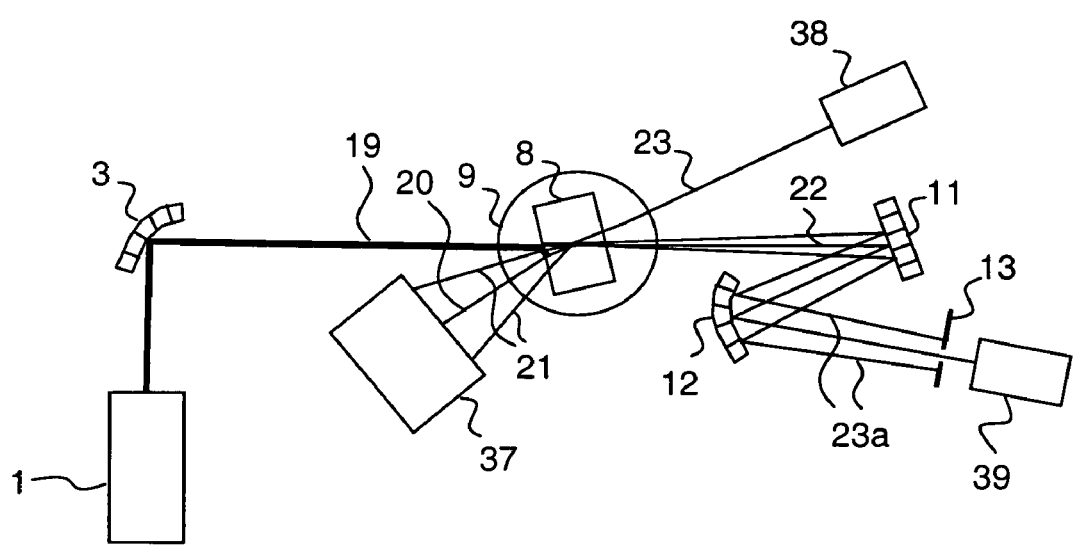
FIG. 6 is a schematic diagram of another embodiment of the new spectrophotometer in accordance with the present invention.

FIG. 6 presents another embodiment of the present invention to acquire the wavelength dependence of the measured signals from the sample assembly 8. A broadband light beam 19 is incident on the sample assembly 8 after collimation by the curved mirror 3. The coherently reflected light beam 20 and diffusely reflected light beams 21 are collected by a spectral imaging photodetector 37, which contains a dispersive device and a two-dimensional imaging photodetector. The dispersive device separates different spectral components of each of the reflected light beams in a direction perpendicular to the plane of the beams while the imaging photodetector records each reflected light beam along one direction of its surface as a function of wavelength and intensity signals of different reflected light beams at one wavelength along another direction. This type of spectral imaging photodetectors are well known to those in the art. The sample assembly 8 can be rotated by the sample assembly table 9 so that the coherently reflected light beam 20 can be acquired at multiple incident angles.

The forwardly scattered light beam 23 and the transmitted light beam 22 are collected by the linear spectral detector 38 and 39, respectively. Each of these linear spectral detectors contains a dispersive device to separate different spectral components of the collected light beam and a linear array photodetector with multiple detecting elements to record the intensity signal of the dispersed light beam at multiple spatial locations as a function of wavelength.

Normalization of the intensity signals of coherently reflected light, diffusely reflected light, collimated transmitted light and diffusely transmitted light from a turbid material sample by the incident light signal at each of the corresponding wavelengths produces the measured signals of $R_c$, $R_d$, $T_c$ and $T_d$ as functions of wavelength, respectively. A major benefit of the embodiment as depicted in FIG. 6 lies in its high speed of signal acquisition.

That which is claimed is:

1. A spectrophotometric apparatus for measurement of optical signals from a turbid material sample as functions of light wavelength which comprises:
   a source for producing a monochromatic light beam of adjustable wavelength;
   a means to illuminate said sample at a plurality of incident angles;
   detecting means spatially located on the front surface side of said sample to measure optical signals of coherent reflectance and diffuse reflectance of said sample; and
   detecting means spatially located on the rear surface side of said sample to measure optical signals of collimated transmittance and diffuse transmittance of said sample.

2. The spectrophotometric apparatus of claim 1, wherein the source comprises a broadband light source; a monochromater; a beam shaping device and a beam splitter with a photodetector to produce a monochromatic light beam of adjustable wavelength incident on said sample and to measure the incident light intensity signal.

3. The spectrophotometric apparatus of claim 2, wherein the monochromater comprises a beam shaping device; a diffraction grating and narrow slits to produce a monochromatic light beam of adjustable wavelength.

4. The spectrophotometric apparatus of claim 1, wherein a means for changing the incident angle includes a device to rotate said sample with respect to the incident light beam.

5. The spectrophotometric apparatus of claim 1, wherein a means for variation of the incident angle includes a device to change the direction of the incident light beam with respect to the said sample.

6. The spectrophotometric apparatus of claim 1, wherein the detecting means spatially located on the front surface side of said sample comprises a linear array photodetector with multiple detecting elements to collect coherently reflected light intensity signal and diffusely reflected light intensity signals which are normalized by the incident light intensity signal to obtain respectively the optical signals of coherent reflectance and diffuse reflectance.

7. The spectrophotometric apparatus of claim 1, wherein the detecting means spatially located on the rear surface side of said sample comprises an optical device to spatially filter out the forwardly scattered light from the collimated transmitted light and a photodetector to detect the collimated transmitted light intensity signal which is normalized by the incident light intensity signal to obtain the optical signal of collimated transmittance.

8. The spectrophotometric apparatus of claim 7, wherein the optical device for spatial filtering of transmitted light comprises a curved mirror and a pinhole or narrow slit to separate the forwardly scattered light from the collimated transmitted light.

9. The spectrophotometric apparatus of claim 1, wherein the detecting means spatially located on the rear surface side of said sample comprises a photodetector to collect diffusely transmitted light intensity signal which is normalized by the incident light intensity signal to obtain the optical signal of diffuse transmittance.

10. A spectrophotometric apparatus for measurement of optical signals from a turbid material sample as functions of light wavelength which comprises:
   a source for producing a broadband light beam;
   a means to illuminate said sample at a plurality of incident angles;
   detecting means spatially located on the front surface side of said sample to measure optical signals of coherent reflectance and diffuse reflectance from said sample as functions of light wavelength; and
   detecting means spatially located on the rear surface side of said sample to measure optical signals of collimated transmittance and diffuse transmittance from said sample as functions of light wavelength.

11. The spectrophotometric apparatus of claim 10, wherein the source comprises a broadband light source and a beam shaping device to produce a light beam of a plurality of wavelength incident on said sample.

12. The spectrophotometric apparatus of claim 10, wherein the detecting means comprises spectral dispersive devices and photodetectors to measure light intensity signals as functions of wavelength.

13. The spectrophotometric apparatus of claim 12, wherein the photodetectors comprise spectral imaging photodetectors to measure light intensity signals of different wavelengths distributed at different spatial locations.

14. A method for determination of optical parameters characterizing a turbid material sample from measured optical signals, the steps comprising:
   (a) acquiring measured signals of coherent reflectance at a plurality of incident angle and determining the real refractive index of said sample;
   (b) acquiring a measured signal of collimated transmittance and determining the attenuation coefficient of said sample;
   (c) acquiring measured signals of diffuse reflectance and diffuse transmittance; and
   (d) obtaining calculated signals of diffuse reflectance and diffuse transmittance and determining the absorption coefficient, scattering coefficient and anisotropy factor of said sample.

15. The method of claim 14, wherein the real refractive index of said sample is determined in step (a) from the measured signals of coherent reflectance at a plurality of incident angle based on the Fresnel equation.

16. The method of claim 14, wherein the attenuation coefficient of said sample is determined in step (b) from the measured signal of collimated transmittance based on the Beer's law using the input data of reflection loss and sample thickness along the direction of transmitted light beam.

17. The method of claim 14, wherein the absorption coefficient, scattering coefficient and anisotropy factor are determined in step (c) and step (d) from the measured signals of diffuse reflectance and diffuse transmittance and the calculated signals of diffuse reflectance and diffuse transmittance based on the numerical solution of the boundary-value problem defined by the radiative transfer equation and Fresnel equation using the input data of the real refractive index and attenuation coefficient.

18. The method of claim 14, wherein the absorption coefficient, scattering coefficient and anisotropy factor are determined in step (c) and step (d) from the measured signals of diffuse reflectance and diffuse transmittance and the calculated signals of diffuse reflectance and diffuse transmittance based on the statistical method of Monte Carlo simulation within the framework of the radiative transfer equation and Fresnel equation using the input data of the real refractive index and attenuation coefficient.

19. The method of claim 14, wherein the optical parameters are determined from the measured signals by comparing the difference between calculated signals and measured signals in terms of error functions and reducing the error functions to values less than the experimental errors of the measured signals.

* * * * *